(12) United States Patent  
Han et al.

(10) Patent No.: US 11,058,374 B2  
(45) Date of Patent: Jul. 13, 2021

(54) RADIATION DETECTOR AND RADIOGRAPHY APPARATUS HAVING THE SAME

(71) Applicant: DRTECH CORP, Seongnam-Si (KR)

(72) Inventors: Seung Zoo Han, Seoul (KR); Jin Hyun Choi, Suwon-Si (KR); Choul Woo Shin, Seongnam-Si (KR); Jung Seok Kim, Seongnam-Si (KR); Young Jong Oh, Yongin-Si (KR); Jae Dong Lee, Seongnam-Si (KR)

(73) Assignee: DRTECH CORP

( * ) Notice: Subject to any disclaimer, the term of this patent is extended or adjusted under 35 U.S.C. 154(b) by 1233 days.

(21) Appl. No.: 14/904,949

(22) PCT Filed: Nov. 24, 2015

(86) PCT No.: PCT/KR2015/012655  
§ 371 (c)(1),  
(2) Date: Jan. 13, 2016

(87) PCT Pub. No.: WO2017/086518  
PCT Pub. Date: May 26, 2017

(65) Prior Publication Data  
US 2017/0281103 A1  Oct. 5, 2017

(30) Foreign Application Priority Data  
Nov. 16, 2015  (KR) .................. 10-2015-0160713

(51) Int. Cl.  
*A61B 6/00* (2006.01)  
*A61B 5/00* (2006.01)  
*A61B 6/04* (2006.01)

(52) U.S. Cl.  
CPC .......... *A61B 6/4283* (2013.01); *A61B 5/0091* (2013.01); *A61B 6/00* (2013.01);  
(Continued)

(58) Field of Classification Search  
None  
See application file for complete search history.

(56) References Cited

U.S. PATENT DOCUMENTS

| | | | |
|---|---|---|---|
| 2010/0034351 A1* | 2/2010 | Yanagita | A61B 6/4216 378/62 |
| 2013/0048866 A1* | 2/2013 | Nishino | G01T 1/2018 250/366 |

(Continued)

FOREIGN PATENT DOCUMENTS

| CN | 1190467 A | 8/1998 |
|---|---|---|
| CN | 1203695 A | 12/1998 |

(Continued)

OTHER PUBLICATIONS

International Search Report for PCT/KR2015/012655 dated May 9, 2016.

(Continued)

*Primary Examiner* — Oommen Jacob  
*Assistant Examiner* — Shahdeep Mohammed  
(74) *Attorney, Agent, or Firm* — Renaissance IP Law Group LLP

(57) ABSTRACT

The present invention proposes a radiation detector including a housing, a radiation detection panel accommodated in the housing and converting radiation incident from the outside of the housing into an electric signal, a printed circuit board electrically connected to the radiation detection panel and an intermediate plate that is disposed between the radiation detection panel and the printed circuit board, supports the radiation detection panel, and is electrically connected to the ground line of the printed circuit board, wherein the intermediate plate is transmissive to the radiation.

25 Claims, 5 Drawing Sheets

(52) U.S. Cl.
CPC ............ *A61B 6/0414* (2013.01); *A61B 6/40* (2013.01); *A61B 6/4258* (2013.01); *A61B 6/502* (2013.01); *A61B 6/5258* (2013.01); *A61B 6/542* (2013.01); *A61B 6/545* (2013.01)

(56) References Cited

U.S. PATENT DOCUMENTS

| | | | | |
|---|---|---|---|---|
| 2013/0058453 | A1* | 3/2013 | Kuwabara | A61B 6/542 378/62 |
| 2013/0140465 | A1* | 6/2013 | Nishinou | G03B 42/02 250/366 |
| 2013/0301808 | A1* | 11/2013 | Koyanagi | G03B 42/04 378/189 |
| 2014/0027636 | A1 | 1/2014 | Watano | |

FOREIGN PATENT DOCUMENTS

| | | |
|---|---|---|
| CN | 102481131 A | 5/2012 |
| CN | 106707324 A | 5/2017 |
| EP | 2437118 A1 | 4/2012 |
| EP | 2565680 A1 | 3/2013 |
| JP | 20056806 A | 1/2005 |
| JP | 2005055564 A | 3/2005 |
| JP | 2011058999 A | 3/2011 |
| JP | 2012073186 A | 4/2012 |
| JP | 2012135524 A | 7/2012 |
| JP | 2014025846 A | 2/2014 |
| JP | 5591682 B2 | 9/2014 |
| JP | 2014225525 A | 12/2014 |
| KR | 20100004949 A | 1/2010 |
| KR | 20110044903 A | 5/2011 |
| WO | 2008120293 A1 | 10/2008 |
| WO | 2010038877 A1 | 4/2010 |

OTHER PUBLICATIONS

International Search Report and Written Opinion of PCT/KR2015/012655 dated May 9, 2016.
Written Opinion for PCT/KR2015/012655 dated May 9, 2016.
Extended European Search Report for Application No. 15880668.7 dated Jun. 25, 2018.

* cited by examiner

DIRECTION OF INCIDENT X-RAY

RADIATION DETECTOR AND RADIOGRAPHY APPARATUS HAVING THE SAME

TECHNICAL FIELD

The present invention relates to a radiation detector detecting radiation, and a radiography apparatus having the same.

BACKGROUND ART

A radiography apparatus is an apparatus capable of obtaining internal images of an object by using the radiation that was emitted to the object and passed through the object. Since radiation transmissivity differs according to the properties of the materials constituting the object, the intensity of the radiation that passes through the object may be detected to thereby image the internal structure of the object.

Here, due to the influence of noise that is generated from a light-receiving element or a read out integrated circuit (read out IC), and the like, which are included in the radiography apparatus, each sensor cell in a radiation detection panel may output a radiation having a different intensity, even when radiation having the same intensity is incident on the radiation detector in the radiography apparatus. This becomes a source of the noise generated in an image.

Regarding radiography apparatus in the medical field, techniques for obtaining images of objects through a digital radiography (DR) apparatus instead of a computer radiography (CR) apparatus are being widely pursued. Typically, computer radiography mammography cassettes used in computer radiography mammography apparatus are classified according to size as 18×24 cm² (small) or 24×30 cm² (large). Here, instead of the computer radiography mammography cassette, it is necessary for a digital radiography mammography cassette to be installed in the computer radiography mammography apparatus.

In order to insert the digital radiography (DR) mammography cassette into a computer radiography (CR) mammography case in the computer radiography (CR) mammography apparatus, constituent parts need to be integrated within the standardized size of the computer radiography (CR) mammography cassette. As such, when designing the digital radiography (DR) mammography cassette, it is necessary to consider the effect that the electrical noise generated due to the highly dense mounting of the integrated elements has on the images.

Meanwhile, when the radiography apparatus is operated, a large amount of heat is generated in elements, in particular, the read out integrated circuit, mounted on a printed circuit board. When such heat is transported to the radiation detection panel, the operating temperature of the radiation detection panel increases. Accordingly, since the dark current in a photoelectric conversion element and leakage current in a thin film transistor (TFT) increase, and the amount of fixed noise changes, there is a problem of being a cause of non-uniformity in the image.

(Patent Document) Japanese Publication of Patent Application No. 2005006806A

DISCLOSURE OF THE INVENTION

Technical Problem

The present invention provides a radiation detector providing an intermediate plate shielding noise that is generated from elements mounted on a printed circuit board of the radiation detector, and also provides a radiography apparatus including the radiation detector.

Technical Solution

A radiation detector according to an embodiment of the present invention includes a housing; a radiation detection panel accommodated in the housing and converting radiation incident from the outside of the housing into an electric signal; a printed circuit board electrically connected to the radiation detection panel; and an intermediate plate that is disposed between the radiation detection panel and the printed circuit board, supports the radiation detection panel, and is electrically connected to the ground line of the printed circuit board, wherein the intermediate plate is transmissive to the radiation.

The intermediate plate may include an electrically conductive first metal layer that is electrically connected to the ground line of the printed circuit board; and a base plate supporting the first metal layer.

The absolute radiation transmittance of the intermediate plate may be 30% or higher with respect to the radiation generated by a tube voltage of 20 to 35 kVp.

The intermediate plate may include at least one of carbon fiber or plastic, and the first metal layer may be provided on the back surface of the base plate.

A plurality of conductive connecting parts provided spaced apart from each other and electrically connecting the first metal layer to the ground line of the printed circuit board may be further included, wherein the conductive connecting part may include a body part connected to the printed circuit board and extending toward the intermediate plate, and a contacting part having a larger cross-sectional area than the body part and forming a contact surface with the first metal layer.

The thermal conductivity of the base plate may be lower than the thermal conductivity of the first metal layer.

The intermediate plate may further include a second metal layer provided on the front surface of the base plate and electrically connected to the first metal layer.

The first metal layer may be electrically connected to the second metal layer at an edge region of the intermediate plate.

The housing may include a frame composed of metal; and a supporting part extending from the frame and supporting the intermediate plate, wherein the supporting part is coupled to the intermediate plate, contacting with the intermediate plate by way of surface contact.

The supporting part may be coupled to the intermediate plate at an edge region of the intermediate plate.

A plurality of electronic components electrically connected to the radiation detection panel may be mounted on both surfaces of the printed circuit board A radiography apparatus according to another embodiment of the present invention may include a radiation generator; the radiation detector such as described above which is detecting radiation emitted from the radiation generator; an automatic exposure control sensor sensing, among radiation emitted from the radiation generator, the radiation passing through the radiation detector; and a controller to control the exposure dose of the radiation emitted from the radiation generator according to the radiation dose sensed by the automatic exposure control sensor.

Advantageous Effects

A radiation detector according to an embodiment of the present invention may minimize ground loop noise by electrically connecting a ground line in a printed circuit board to an intermediate plate in a uniform manner, and emit sufficient radiation on an automatic exposure control sensor by using the intermediate plate capable of transmitting radiation. Therefore, the stable radiation image may be obtained, and a patient who is the object receiving radiation may be protected from an excessive radiation dose through automatic exposure control of the radiation.

A radiation detector according to an embodiment of the present invention may obtain a stable radiation image by providing an intermediate plate, on which a metal layer is formed on the opposite surface (hereinafter referred to as the back surface) to the surface on which radiation is emitted on a base plate, to form a shield for a ground potential connected to a ground line of a printed circuit board, and thereby shield outside noise. Moreover, by electrically connecting the metal layer formed on the back surface of the intermediate plate that is formed as the shield for the ground potential to the ground line of the printed circuit board, the separation distance may be minimized to minimize ground loop noise. When the ground loop noise is minimized, an even more stable radiation image may be obtained.

In addition, in a radiation detector according to an embodiment of the present invention, a metal layer on the back surface of a base plate included in an intermediate plate may be coupled to a frame of a housing such that heat generated in a printed circuit board is effectively released to the outside through conduction. Thus, since the radiation detector according to the present invention is able to shield the heat conducted to a radiation detection panel, image noise that is caused by heat may be removed. Therefore, the radiation detector according to the present invention may obtain an even more stable and sharp radiation image.

Consequently, a radiation detector according to an embodiment of the present invention may be designed as a small, film-type digital radiography (DR) mammography cassette capable of maintaining high robustness and noise tolerance.

MODE FOR CARRYING OUT THE INVENTION

Figure 1:
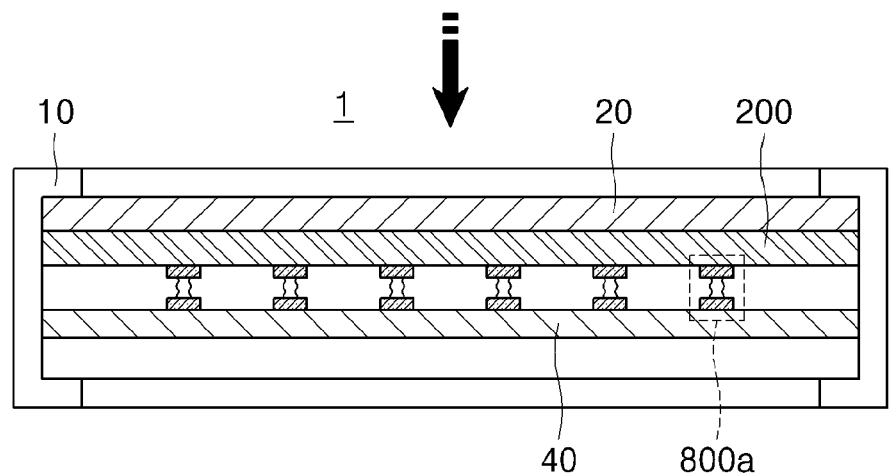
FIG. 1 is a cross-sectional view of a radiation detector according to an embodiment of the present invention.

Hereinafter, specific embodiments will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. In the figures, the dimensions of layers and regions are exaggerated for clarity of illustration. Like reference numerals refer to like elements throughout.

Hereinafter, exemplary embodiments of the present invention are described with reference to the accompanying drawings.

FIG. 1 is a cross-sectional view of a radiation detector 1 according to an embodiment of the present invention. Referring to FIG. 1, the radiation detector 1 according to an embodiment of the present invention may include a housing 1, a radiation detection panel 20, an intermediate plate 200, a printed circuit board 40, and a plurality of conductive connecting parts 800a.

The housing 10 may include an upper cover, a frame, and a lower cover. The upper cover is disposed on a surface on which radiation is incident, and may not only alleviate external shock, but is composed of a material having a very high radiation transmittance and/or a very low radiation absorbance. For example, the upper cover and the lower cover may include carbon, carbon fiber, a carbon compound, glass fiber, a glass fiber-containing composite material, polycarbonate, or a polycarbonate compound. The frame forms the external shape of the radiation detector 1 and protects elements that are accommodated therein. The frame may include a thermally conductive metal having mechanical strength, such as copper, aluminum, or stainless steel.

The radiation detection panel 20 is accommodated in the housing 10 and converting radiation incident from the outside of the housing 10 into an electric signal that can be image signal-processed, and a plurality of switching cell elements and photoelectric conversion elements may be arranged thereon in the form of a matrix. Here, the radiation may be an x-ray, an alpha ray ($\alpha$-ray), a gamma ray ($\gamma$-ray), an electron beam, or an ultraviolet ray (UV-ray), and the like. The radiation detector 1 may be classified as a direct method or an indirect method according to an absorption layer material that absorbs radiation. Materials used in the direct method include amorphous selenium, crystalloid cadmium telluride (CdTe), or a crystalloid cadmium telluride compound. Materials used in the indirect method are known as a scintillator, and representative examples include cesium iodide (CsI) and gadolinium oxysulfide (GdOxSy).

The radiation detector 1 according to an embodiment uses the scintillator-based indirect method. Here, the radiation detection panel 20 includes a pixel circuit board and a light emitting layer. The pixel circuit board is disposed to face the upper cover. The pixel circuit board may include a thin film transistor (TFT) and include a two-dimensional pixel array that constitutes each pixel circuit. Describing the electric signal detection mechanism of the radiation detection panel 20, when radiation reaches the light emitting layer, the light emitting layer emits light signals due to the radiation, and when such light signals are transmitted to a light-receiving element, such as a photodiode, disposed on the pixel circuit, the light-receiving element detects the light signal and converts the light signal into an electric signal.

The light emitting layer is formed above the pixel circuit board. The light emitting layer may be applied as a film to cover the entire pixel array. The light emitting layer according to an embodiment is the scintillator. In this case, the scintillator may be applied on the pixel circuit board or formed with the pixel circuit board. Radiation that passes through an object is converted to visible light through the scintillator, and such visible light is detected by the pixel circuit board as the electric signal.

The radiation detector 1 according to another embodiment uses the direct method by which the electric signal generated by the radiation that passes through the object is detected directly. Here, the radiation detection panel 20 includes the pixel circuit board and a photoconductor. The photoconductor exhibits photoconductivity and may include, for example, amorphous selenium, crystalloid CdTe, or a crystalloid cadmium telluride compound.

The printed circuit board 40 is provided in the housing 10 to supply power to the radiation detection panel 20 in order to control and process and thereby enable an image signal about the object to be output. The electronic components mounted on the printed circuit board 40 generate noise caused by electromagnetic interference (EMI), and lines on the printed circuit board may also cause the propagation and radiation of noise. When the radiation detection panel 20 receives the effects of this noise, noise may also be generated in the radiation image.

Meanwhile, solutions to such noise include reinforcing the ground to stabilize the ground, shielding the noise source, and filtering the noise.

Among these, a method for reinforcing the ground includes forming the ground to be as wide and uniform as possible. This is because, when there are multiple ground points, the ground circuit forms a loop such that a ground loop flows to thereby cause a change in the reference potential. It is necessary for the ground to uniformly be the reference potential (for example, 0 V), and when there are multiple ground points such that the ground loop having a different distance is formed, a case occurs in which, due to influence from the impedance of the line, and the like, the ground point differs from the reference potential. Here, since current flows in the ground circuit, a voltage drop caused by the impedance may occur such that the reference potential is changed.

The intermediate plate 200 is disposed between the radiation detection panel 20 and the printed circuit board 40 to support the radiation detection panel 40, and may include materials that are both light and have excellent physical strength. Moreover, the intermediate plate 200 may be formed as a conductive plate and be electrically connected to the ground line of the printed circuit board 40. By using the intermediate plate to form a shield for the ground potential, the electromagnetic interference noise caused by the electronic components mounted on the printed circuit board 40 may be shielded and the ground may be reinforced to stabilize the ground. Therefore, despite the influence of the electromagnetic interference noise caused by the electronic components mounted on the printed circuit board, the radiation detector 1 is able to obtain a stable image. Thus, the radiation detector 1 may exhibit superb properties related to noise shielding by reinforcing, through the conductive intermediate plate 200, the grounding of the radiation detection panel 20 and the printed circuit board 40.

Ground loop noise is noise that is caused by grounding a device to grounds having different electric potentials. That is, ground loop noise is noise that occurs due to the electric potential difference between grounds becoming different from each other when the ground loop distance is spaced far apart. As described above, the ground must uniformly be the reference potential (for example, 0 V), and when there are multiple ground points such that ground loops having different distances are formed, a case occurs in which, due to the influence of the impedance of the line, and the like, the ground point actually differs from the reference potential. Here, since current flows in the ground circuit such that a voltage drop caused by the impedance occurs to thereby change the reference potential, the ground loop noise is generated. Thus, with respect to display quality, in order to minimize the ground loop noise, the ground potential of the intermediate plate 200 must be uniform with the ground potential of the printed circuit board 40 and the reference potential.

Figure 9:
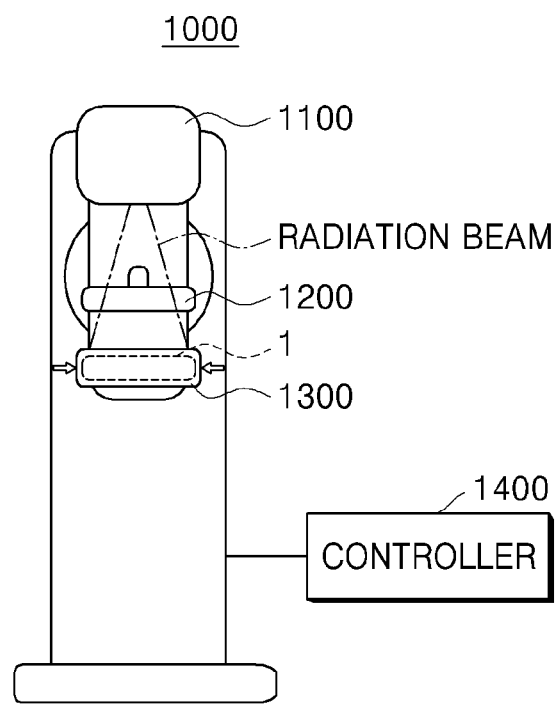
FIG. 9 is a front elevation of a radiography apparatus according to the present invention.
Figure 10:
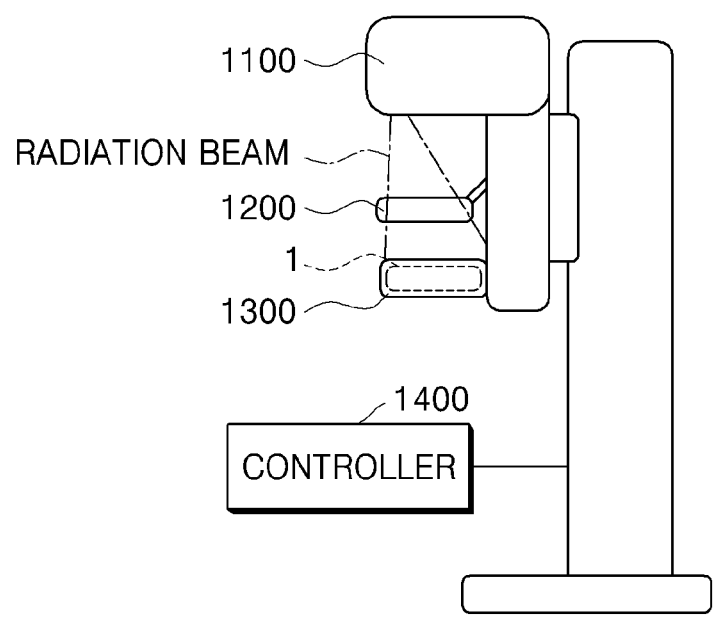
FIG. 10 is a side elevation of a radiography apparatus according to the present invention.

Referring to FIGS. 9 and 10, as described below, when the radiation detector 1 according to the present invention is mounted on a standardized cassette of a computer radiography (CR) apparatus, for mounting efficiency, the electronic components mounted on the printed circuit board 40 may be mounted on both surfaces of the printed circuit board 40. In this case, due to the electronic components mounted on the front surface of the printed circuit board 40, the ground loop noise may not be minimized by disposing the printed circuit board 40 to directly contact the intermediate plate 200. That is, even when the intermediate plate 200 is electrically connected to the ground line of the printed circuit board 40, a separation distance is physically generated between the printed circuit board 40 and the intermediate plate 200. Here, since a ground loop may be formed between the grounds, in order to minimize the ground loop noise, the separation distance between the ground line of the printed circuit board 40 and the intermediate plate 200 must be minimized.

Figure 2:
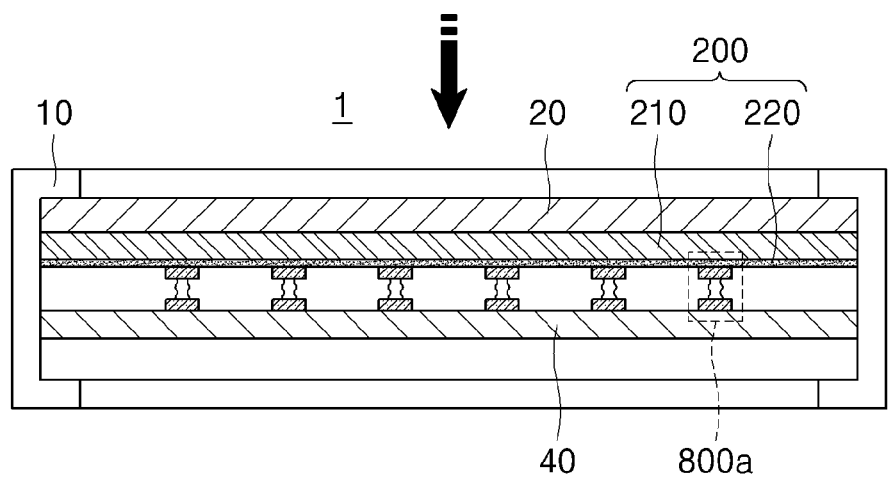
FIG. 2 is a cross-sectional view of a radiation detector according to another embodiment of the present invention.

Moreover, in order to provide ground loop noise stability to the electric signal of the radiation detection panel 20, the intermediate plate 200 must be used as the reference potential of the printed circuit board 40, and the separation distance (that is, the loop distance between the grounds) between the intermediate plate 200 and the printed circuit board must be minimized to thereby minimize the ground loop noise. To realize this, as illustrated in FIG. 2 and described below, the intermediate plate 200 may include, on a surface that faces the printed circuit board 40 and is thus the opposite surface to the surface on which radiation is incident, a metal layer capable of a grounding function. However, it is sufficient for such a metal layer to be included in the intermediate plate and electrically conductive, and the position at which the metal layer is provided need not be particularly limited. Meanwhile, the conductive connecting parts 800a electrically connect the ground line of the printed circuit board 40 to the intermediate plate 200. Detailed description thereof will be given later with reference to FIGS. 4 to 6.

FIG. 2 is a cross-sectional view of a radiation detector 1 according to another embodiment of the present invention. Referring to FIG. 2, the intermediate plate 200 may include an electrically conductive first metal layer 220 that is electrically connected to the ground line of the printed circuit board; and a base plate 210 supporting the first metal layer. That is, the intermediate plate 200 may include the electrically conductive first metal layer 220 that provides a grounding function, and the base plate 210 that provides mechanical strength and includes at least one of a carbon fiber or a plastic that has excellent radiation transmittance, such as carbon fiber reinforced plastic CFRP, polycarbonate PC, polyimide, polycarbonate ABS (PC-ABS), polypropylene (PP), polyethylene (PE), or acrylic. Meanwhile, the first metal layer 220 may be provided on the back surface of the base plate 210, but the position at which the first metal layer 220 is formed with respect to the base plate 220 need not be particularly limited.

In particular, the carbon fiber layer or the carbon fiber reinforced plastic is the material having excellent radiation transmittance and physical strength and may thus be used as the base plate 210 of the intermediate plate 200. The first metal layer 220 may be attached to the base plate 210 in the form of a foil, or be formed to a uniform thickness through vacuum deposition or various plating methods, and the like. The first metal layer 220 formed on the back surface of the intermediate plate 200 may be electrically connected to the ground line of the printed circuit board 40 through the plurality of conductive connecting parts 800a. Detailed description thereof is given below with reference to FIGS. 4 to 6.

As described in FIG. 1, in order to minimize the ground loop noise, which is the noise caused by the potential difference due to the distance between the grounds, the ground potential of the first metal layer 220 must be uniform with the ground potential of the printed circuit board 40 and the reference potential (for example, 0 V). Here, the ground potential of the radiation detection panel 20 may also be uniform with the ground potential of the printed circuit board 40 and the reference potential. Moreover, the first metal layer 220 may be provided on the back surface of the intermediate plate 200 to minimize the separation distance with the printed circuit board 40. Thus, since the uniformity of the potential difference may be maximized by minimizing the loop distance between the grounds, the ground loop noise may be reduced. To realize this, a large number of the conductive connecting parts 800a may be uniformly connected to the ground line of the printed circuit board 40 and to the first metal layer 220. Moreover, the ground must be electrically connected to all of the frame of the housing 10, the first metal layer 220, the ground line of the printed circuit board 40, and the ground line of the radiation detection panel 20. Here, the electric potential of the intermediate plate 200, as the reference potential, must be uniform with the ground potential of the printed circuit board 40 and the ground potential of the radiation detection panel 20 in order to reduce the ground loop noise.

Furthermore, when an automatic exposure control sensor (AEC) is provided on the back surface of the intermediate plate 200, the intermediate plate 200 must be a radiation transmissive member capable of transmitting radiation to the automatic exposure control sensor. Thus, as described below with reference to FIGS. 9 and 10, when using the radiation detector 1 as the cassette of a computer radiography (CR) mammography apparatus, the intermediate plate 200 must be a material having a high radiation transmittance in order to sufficiently transmit radiation to the automatic exposure control sensor (AEC). The automatic exposure control sensor 1300 may generate a control signal that controls the radiant exposure by detecting the radiation that is emitted from a radiation generator 1100 and passes through the object and the radiation detector 1. Here, when the automatic exposure control sensor 1300 is disposed on the back surface of the radiation detector 1, detection of the radiation by the electronic components such as the read out integrated circuit may be hindered, and thus the automatic exposure control sensor 1300 may be disposed in a space other than the area in which the electronic components are provided.

Here, radiation transmissivity indicates not only cases in which the incident radiation completely passes through as it is (transmittance of 100%), but also includes cases in which the incident radiation partially passes through. When the transmittance of the intermediate plate 200 is equal to or higher than a designated transmittance, the radiation may be reliably detected by the typical automatic exposure control sensor (AEC sensor) disposed on the back surface of the radiation detector 1. Thus, the intermediate plate 200 must be the radiation transmissive member, and when the first metal layer 210 is formed on the back surface of the intermediate plate 200, the first metal plate 210 must be composed of a thickness and material that can transmit the radiation.

The radiation generator that is used in a therapeutic radiography apparatus and generates radiation generates radiation when a high acceleration voltage (tube voltage) is applied to a radiation tube such that electrons are accelerated to impact a target provided in the radiation tube. In a typical therapeutic radiography apparatus, a tube voltage of 70 to 100 kVp is applied, but in a radiography apparatus configured for mammography, since radiation is emitted on soft tissue in the breast, which has a much lower density than bone, a low transmittance tube voltage of 20 to 35 kVp is used to detect small cancer cells, which have a small density difference with the surrounding tissue.

Moreover, even though the distribution of breast tissue typically differs according to age, since the structure of tissue is different for each individual, it is difficult to apply an imaging condition relying on only the compressed breast thickness. Existing imaging data may be used, but since the condition of the patient's breast may change due to the hormonal state or age, and the like, and the imaging conditions may also be different, the automatic exposure control (AEC) sensor that automatically controls the radiation dose is necessarily inserted in the radiography apparatus used for mammography. Moreover, when the AEC sensor is provided above (or in front of) the radiation detector, since the radiation is impeded by the AEC sensor before reaching the radiation detector, and the radiography apparatus that is configured for mammography uses a low tube voltage of 20 to 35 kVp, the AEC sensor must be inserted below (or to the back of) the radiation detector.

Table 1 shows the absolute radiation transmittance and the effective radiation transmittance of the intermediate plate 200, which were detected by changing the thickness of the first metal layer 220 of the intermediate plate 200 according to the present invention. Here, a tube voltage of 28 kVp was applied in order to generate radiation in the radiation generator and thereby emit electrons on a molybdenum target fitted with a 0.03 mm molybdenum filter in the radiation tube.

The absolute radiation transmittance is the ratio of the radiation dose that passes through the intermediate plate to the radiation dose incident on the intermediate plate 200 after the radiation generated in the radiation generator passes through free space (that is, air or vacuum). Meanwhile, in the actual radiography apparatus, since a human body and the radiation detection panel in the radiation detector are disposed above the intermediate plate, the radiation generated in the radiation generator passes through the human body and the radiation detection panel before being incident on the intermediate plate. Consequently, in order to more appropriately simulate actual situations, the effective radiation transmittance, which is the ratio of the radiation dose that passes through the intermediate plate to the radiation dose incident on the intermediate plate after passing through a 40 mm polymethyl methacrylate (PMMA) standard phantom (which is similar to the human breast) and the radiation detection panel, was detected.

TABLE 1

| Al thickness (μm) | Absolute radiation transmittance (%) | Effective radiation transmittance (%) |
|---|---|---|
| 0 | 100 | 100 |
| 50 | 91.7555 | 94.1743 |
| 100 | 83.7205 | 91.26144 |
| 150 | 76.8908 | 89.31756 |
| 200 | 70.5677 | 85.19201 |
| 250 | 65.0480 | 83.48591 |
| 300 | 60.1747 | 80.34716 |
| 350 | 55.7904 | 77.19058 |
| 400 | 51.7729 | 74.75924 |
| 450 | 48.1729 | 72.56569 |
| 500 | 44.793 | 69.65878 |
| 550 | 41.1249 | 66.25253 |
| 600 | 37.6734 | 65.2895 |
| 650 | 34.6114 | 63.10783 |
| 700 | 31.724 | 60.92022 |
| 750 | 29.1214 | 59.23196 |
| 800 | 26.7249 | 57.28213 |
| 850 | 24.1604 | 55.88043 |
| 900 | 22.2509 | 54.43871 |
| 950 | 20.4989 | 53.08519 |
| 1000 | 18.8913 | 51.68578 |

As the thickness of an aluminum layer, which is the first metal layer, increases, the radiation is absorbed or reflected by the first metal layer and thus cannot pass through the first metal layer. Therefore, both the absolute radiation transmittance and the effective radiation transmittance become lower, and it may also be observed that there is a difference in the absolute radiation transmittance and effective radiation transmittance with respect to the first metal layer that has the same thickness. Since aluminum is easily formed directly into a thin film or processed into the shape of an easily attachable foil, is easy to obtain, and has a high transmissivity and electrical conductivity, aluminum may be used as the first metal layer, but the first metal layer is not limited to a particular material.

The effective radiation transmittance is based on the radiation dose incident on the intermediate plate after passing through the standard phantom and the radiation detection panel. This is because the average photon energy of the radiation that is incident on the intermediate plate when measuring the effective radiation transmittance is higher than that of the radiation incident on the intermediate plate when measuring the absolute radiation transmittance (that is, radiation photons are already absorbed while passing through the standard phantom and the radiation detection panel, and thus do not participate in the radiation transmittance of the intermediate plate). For example, in the case of the 750 μm thick aluminum first metal layer, the absolute transmittance is 29.1214%, but in actual radiation detection conditions the 750 μm thick aluminum first metal layer may be observed to exhibit the high effective radiation transmittance of about 60%. Consequently, it is desirable that the intermediate plate be characterized based on specifying the absolute radiation transmittance rather than the effective radiation transmittance, which is highly influenced by conditions prior to incidence on the intermediate plate.

In order to apply the radiation detector according to the present invention instead of a cassette-type film in the radiography apparatus configured for use in mammography, it is necessary for a lower limit to be determined at which the automatic exposure control sensor (AEC sensor) provided behind the radiation detector is able to reliably detect the radiation and control the radiation dose. Here, since an x-ray generator of the radiation detector configured for use in mammography uses a tube voltage of 20 to 35 kVp, the radiation transmittance of the intermediate plate must be determined in terms of the tube voltage of 20 to 35 kVp.

Since the base plate (for example, the base plate composed of carbon fiber) included in the intermediate plate has a radiation transmittance approaching 100%, the radiation transmittance of the intermediate plate is determined by the first metal layer. Thus, as shown in FIG. 2, the values of quantity of tube electric charge (mAs), exposure dose, and average glandular dose were measured by changing the thickness of the first metal layer 220 of the intermediate plate 200. The tube voltage applied to the radiation generator was 28 kVp, and the human breast-emulating 40 mm polymethyl methacrylate (PMMA) standard phantom and the automatic exposure control sensor (AEC sensor) were respectively disposed above and below the radiation detector. The aluminum layer was selected as the first metal layer, but the first metal layer is not particularly limited by the material thereof.

TABLE 2

| Al thickness (μm) | Absolute radiation thickness (%) | Quantity of tube electric charge (mAs) | Exposure dose (mGy) | Average glandular dose (mGy) |
|---|---|---|---|---|
| 0 | 100 | 76 | 7.55 | 1.634786 |
| 50 | 91.7555 | 80 | 7.95 | 1.721398 |
| 100 | 83.7205 | 83 | 8.25 | 1.786356 |
| 150 | 76.8908 | 89 | 8.84 | 1.914108 |
| 200 | 70.5677 | 92 | 9.14 | 1.979066 |
| 250 | 65.0480 | 96 | 9.54 | 2.065677 |
| 300 | 60.1747 | 100 | 9.94 | 2.152288 |
| 350 | 55.7904 | 104 | 10.34 | 2.2389 |
| 400 | 51.7729 | 109 | 10.83 | 2.344998 |
| 450 | 48.1729 | 114 | 11.33 | 2.453262 |
| 500 | 44.7930 | 119 | 11.83 | 2.561526 |
| 550 | 41.1249 | 123 | 12.22 | 2.645972 |
| 600 | 37.6734 | 127 | 12.62 | 2.732583 |
| 650 | 34.6114 | 131 | 13.02 | 2.819195 |
| 700 | 31.7240 | 135 | 13.42 | 2.905806 |
| 750 | 29.1214 | 139 | 13.81 | 2.990252 |
| 800 | 26.7249 | 141 | 14.01 | 3.033557 |
| 850 | 24.1604 | 144 | 14.31 | 3.098516 |
| 900 | 22.2509 | 147 | 14.61 | 3.163474 |
| 950 | 20.4989 | 149 | 14.80 | 3.204614 |
| 1000 | 18.8913 | 152 | 15.10 | 3.269573 |

Here, the quantity of tube electric charge (mAs) is the total quantity of electrons that are made to impact the metal target in order generate the radiation, and is the product of the amount of the current (mA) generated when electrons are accelerated to emit the radiation multiplied by the emission time (s). Consequently, there is a linearly proportional relationship between the mAs value and the exposure dose. Typically, the radiography apparatus used in mammography is configured such that when a constant current is applied to generate radiation and emit the radiation on the human body that is the subject of examination and the radiation detector; and the radiation that passed through the human body and the radiation detector is sensed to be the radiation dose set by the automatic exposure control (AEC) sensor; the emission of radiation is terminated. In the present invention, the radiation dose level that is read in the AEC sensor to regulate the radiation dose to a constant level is set to the minimum such that the exposure dose regulated by the AEC is minimized. Moreover, the mAs value was measured according to the thickness of the first metal layer, starting from when emission of the radiation at a fixed tube voltage (for example, of 28 kVp) began, up to when emission of the radiation was terminated by the automatic exposure control sensor (AEC sensor). The exposure dose indicates the dose of the radiation emitted by the radiation tube to correspond to the measured mAs value, and, among the exposure dose, the average glandular dose is the dose of the radiation absorbed in the breast.

As observed in Table 1, the radiation dose that passes through the first metal layer decreases as the thickness of the first metal layer increases. Conversely, the automatic exposure control sensor (AEC sensor) is provided behind the radiation detector such that the amount of radiation exposure is regulated according to a preset value by detecting the radiation that passes through the radiation detector to reach the AEC sensor. Thus, since the radiation dose reaching the AEC sensor decreases as the thickness of the first metal layer increases, the radiation tube is controlled such that a greater radiation dose is emitted (when the sensitivity and set value of the AEC sensor are identical). Typically, increasing the emitted radiation dose may be performed by maintaining the tube current (mA) applied to the radiation tube and increasing the emission time (s) (thus, increasing the mAs value). The measured dose in Table 1 was set to minimize the set value of the dose that causes the AEC sensor to terminate emission such that the minimum radiation dose was emitted.

Therefore, when the absolute radiation transmittance of the intermediate plate (or the first metal layer) is too low, the radiation dose reaching the AEC sensor is too low, and thus the AEC sensor is unable to sense the radiation dose that was preset in order to generate the command to stop emitting radiation. Thus, when the radiation dose reaching the AEC sensor is too low, the emission time (s) must be extended to enable the radiation dose sensed in the AEC sensor to reach the preset radiation dose, but due to limitations in stability, the radiography apparatus may hit an emission time limit such that regulation of the radiation dose through the AEC sensor is impossible. Moreover, when the radiation dose reaching the AEC sensor is decreased even further, the radiation dose may be below even the minimum radiation dose that can be sensed, and thus the AEC sensor may be unable to detect the radiation.

That is, when the absolute radiation transmittance of the intermediate plate (or the first metal layer) is too low, the radiation dose that passes through the radiation detector to reach the automatic exposure control sensor (AEC sensor) is reduced to a level that cannot be detected through calibration of the AEC sensor, and in extreme cases the AEC sensor is unable to detect the radiation. Therefore, in order to sufficiently regulate the radiation dose even when imaging a breast that has a higher density and is thicker than the breast that is emulated by the 40 mm thick PMMA standard phantom, at least an appropriate level of the absolute radiation transmittance must be achieved. It was observed through the emulation test that the emission of radiation was terminated when the radiation dose, which passed through the panel other than the intermediate plate, the 40 mm thick PMMA standard phantom, and the respective intermediate plate according to transmittance, reached 2.7 µGy (set radiation dose). As described above, since the set value of the dose that causes the AEC sensor to terminate emission is set to be minimized such that the minimum radiation dose is emitted, this value is the lowest set value at which the AEC sensor may regulate the termination of the emission of the radiation. When imaging a breast that is lower in density and thinner than the 40 mm thick PMMA standard phantom, since the radiation dose reaching the AEC sensor is greater, there is no limitation due to the low actual radiation, but when imaging a breast that is higher in density and thicker, there is a concern that an excessive dose may be emitted on the human body.

Thus, in the present invention, the radiation dose reaching the AEC sensor is sufficient, and thus when a tube voltage of 20 to 35 kVp (for example, 28 kVp) is used in order to reliably perform regulation of the emitted radiation dose, the intermediate plate according to the present invention may have an absolute radiation transmittance of at least 30% (or an effective radiation transmittance of at least 60%). The absolute radiation transmittance (or effective radiation transmittance) of this intermediate plate is obviously below 100%.

Meanwhile, in the case of the radiography apparatus to be used in mammography for imaging breasts, when the average glandular dose, which is the radiation to which the breast is exposed or that the breast absorbs, becomes excessive, there may be side effects related to stability, such as the occurrence of breast cancer, and thus the recommended average glandular dose is strictly regulated by each country. Domestically, the recommended average glandular dose is 3.0 mGy, and the recommended average glandular dose may be satisfied when the absolute radiation transmittance of the intermediate plate according to the present invention is at least 30%. Meanwhile, in countries recommending an even lower average glandular dose (for example, the recommended average glandular dose in Europe is 2.0 mGy), in order to allow a sufficient dose to reach the AEC sensor such that the AEC sensor is able to regulate and thereby cause the radiation generator to emit an appropriate dose, the radiation transmittance must be at least a particular transmittance (for Europe, a absolute radiation transmittance of at least 70%) because when the absolute radiation transmittance of the intermediate plate is below the particular value, the AEC sensor cannot be calibrated.

In the above embodiment, when the tube voltage of 28 kVp is applied in the tube, the radiation having an energy of 0 to 28 keV is emitted. Since the energy of the radiation (photon) changes according to the applied tube voltage, when the tube voltage changes, the absolute radiation transmittance and effective radiation transmittance of the intermediate plate are also changed. Consequently, the lower limit of the absolute radiation transmittance that must be satisfied by the intermediate plate according to the present invention must be provided with the applied tube voltage (for example 20 to 35 kVp). That is, in the case of the radiation detector used in the radiography apparatus configured for mammography, the absolute radiation transmittance of at least 30% is sufficient for the intermediate plate with respect to the radiation generated by the tube voltage of 20 to 35 kVp, but in the case of the typical radiography apparatus, since the tube voltage higher than 35 kVp is applied such that the radiation having a high energy is easily transmitted, it is acceptable for the absolute radiation transmittance to be lower than 30%.

When using the aluminum layer as the first metal layer, the intermediate plate having the absolute radiation transmittance of at least 30% (or the effective radiation transmittance of at least 60%) with respect to the radiation generated by the tube voltage of 20 to 35 kVp (for example, 28 kVp) may include the aluminum layer having a thickness of 750 µm or less. Here, as described below, when the intermediate plate further includes a second metal layer provided on the front surface, the combined thickness of the first metal layer (aluminum layer) and the second metal layer (aluminum layer) may be 750 μm or less. This is because aluminum (Al), when being fabricated into the first metal layer 220, is easily fabricated by a process into the foil shape, is easily obtained, and has high radiation transmittance and electrical conductivity.

Meanwhile, the aluminum layer was used as the first metal layer in the above description of the intermediate plate according to the present invention, but the present invention may not be particularly limited by the material forming the first metal layer. Any metal material and thickness may be used in which the intermediate plate has the absolute radiation transmittance of at least 30% (or the effective radiation transmittance of at least 60%) with respect to the radiation generated by the tube voltage of 20 to 35 kVp (for example, 28 kVp).

Tables 3 and 4 are tables showing the results of simulating the absolute radiation transmittance according to the respective thickness (μm) of the first metal layer 210 material for an x-ray having 20 KeV of energy. When the tube voltage is 28 kVp, a photon (or radiation) having 0 to 28 keV of energy is emitted, and the photon having a high energy of 20 keV was selected for the simulation in order to exclude the influence of low energy photons that are absorbed or reflected by the standard phantom and radiation detection panel, which are disposed to the front of the intermediate plate. Here, metals having atomic numbers higher than tungsten (W: atomic number of 74) were excluded because such metals may be expensive like platinum (Pt: atomic number of 78) or be a toxic material, and also have a low transmittance.

TABLE 3

| | Thickness (μm) | | |
|---|---|---|---|
| | 1000 | 500 | 100 |
| Mg (#12) | 61.87% | 78.65% | 95.31% |
| Al (#13) | 39.49% | 62.84% | 91.13% |
| Cr (#24) | 0.00% | 0.07% | 23.10% |
| Cu (#29) | 0.00% | 0.00% | 4.91% |
| Ni (#28) | 0.00% | 0.00% | 5.68% |
| W (#74) | 0.00% | 0.00% | 0.92% |

TABLE 4

| | Thickness (μm) | | |
|---|---|---|---|
| | 5 | 0.5 | 0.05 |
| Mg (#12) | 99.76% | 99.98% | 100.00% |
| Al (#13) | 99.54% | 99.95% | 100.00% |
| Cr (#24) | 92.94% | 99.27% | 99.93% |
| Cu (#29) | 86.01% | 98.50% | 99.85% |
| Ni (#28) | 86.64% | 98.58% | 99.86% |
| W (#74) | 79.08% | 97.68% | 99.77% |

Meanwhile, for the aluminum layer having the same thickness, the measured absolute radiation transmittance in Table 1 (44.793%) differs from the simulated absolute radiation transmittance in Table 3 (62.84%), but this is due to using the tube voltage of 28 kVp in the measurement while conversely using the energy of 20 keV in the simulation. That is, since the radiation emitted due to the tube voltage of 28 kVp includes numerous photons having an energy lower than 20 keV, the actual measured absolute radiation transmittance is lower than the absolute radiation transmittance obtained when simulating with the photons having 20 keV of energy.

As observed in Table 3, the thickness of not only aluminum but various metals may be adjusted to obtain various absolute radiation transmittances. Large metals having a higher atomic number than aluminum transmit almost no radiation at a thickness of 500 μm, but are observed to have an extremely high absolute radiation transmittance when the thickness is reduced.

As described above, without being particularly limited by the metal or thickness, the intermediate plate having the absolute radiation transmittance of at least 30% (or the effective radiation transmittance of at least 60%) with respect to the radiation generated by the tube voltage of 20 to 35 kVp (for example, 28 kVp) is sufficient. Moreover, the thickness of the first metal layer in the intermediate plate may be thinner or equal to the thickness of the intermediate plate that has the absolute radiation transmittance of at least 30% with respect to the radiation generated by the tube voltage of 20 to 35 kVp. The thickness when the absolute radiation transmittance of this intermediate plate is at least 30% may be changed according to the material forming the first metal layer.

Meanwhile, in order to increase the absolute radiation transmittance of the intermediate plate according to the present invention, a predetermined portion of the first metal layer may be removed, or the first metal layer may be patterned (for example, the first metal layer in the form of a mesh) by forming an open part to expose the surface of the base plate. When the typical radiation or the radiation that was changed into light by a light converting layer reaches the first metal layer, the radiation or light may be reflected by the first metal layer to be reincident on the radiation detection panel and thereby included in the electric signal generated in the radiation detection panel. When the portion of the first metal layer is removed or patterned in order to increase the absolute radiation transmittance of the intermediate plate, the reflected radiation or light differs according to region in the intermediate plate such that a problem in which the electric signal generated in the radiation detection panel is distorted may occur. Conversely, when the first metal layer according to the present invention is formed in the shape of a blanket film that excludes the removed part or the open part, and the like, the radiation or light is uniformly reflected over the entire surface of the intermediate plate such that the problem due to the non-uniformity according to region in the first metal layer may be overcome. When the reflection, which is due to the intermediate plate (first metal layer), of the radiation or light does not occur or has an insignificant influence, the portion of the first metal layer may be removed or patterned, and, of course, may also be formed into the shape of the blanket film.

The intermediate plate 200 of the present invention not only has radiation transmissivity, but the ground potential of the intermediate plate is also required to be uniform with the ground potential of the printed circuit board and the reference potential (for example, 0 V) in order to minimize the ground loop noise in the printed circuit board, and to realize this, the intermediate plate must be sufficiently conductive. The upper limit to the thickness of the first metal layer is determined by the absolute radiation transmittance that is required in the intermediate plate (at least 35% with respect to the radiation generated by the tube voltage of 20 to 35 kVp), but conversely, the lower limit of the first metal layer may be determined by the thickness of the first metal layer that is capable of providing sufficient conductivity to the intermediate plate.

When the thickness of the first metal layer is too thin, even though the absolute radiation transmittance is high, due to the thickness being thin, even when a thin film is formed using a thin film process the boundary properties dominate the material properties of the thin film such that the electrical conductivity required for a stable ground may not be obtained. Therefore, in terms of the radiation transmittance, it is advantageous for the first metal layer of the intermediate plate to be thin, but the first metal layer must be formed to be at least a certain thickness in order for the ground to be stable. Accordingly, in the present invention, the first metal layer 220 of the intermediate plate may have a thickness of 0.03 to 1000 μm in order to enable the intermediate plate to have the absolute radiation transmittance of at least 30% with respect to the radiation generated by the tube voltage of 20 to 35 kVp (for example, 28 kVp), and also have the high electrical conductivity and the stable grounding.

Figure 3:
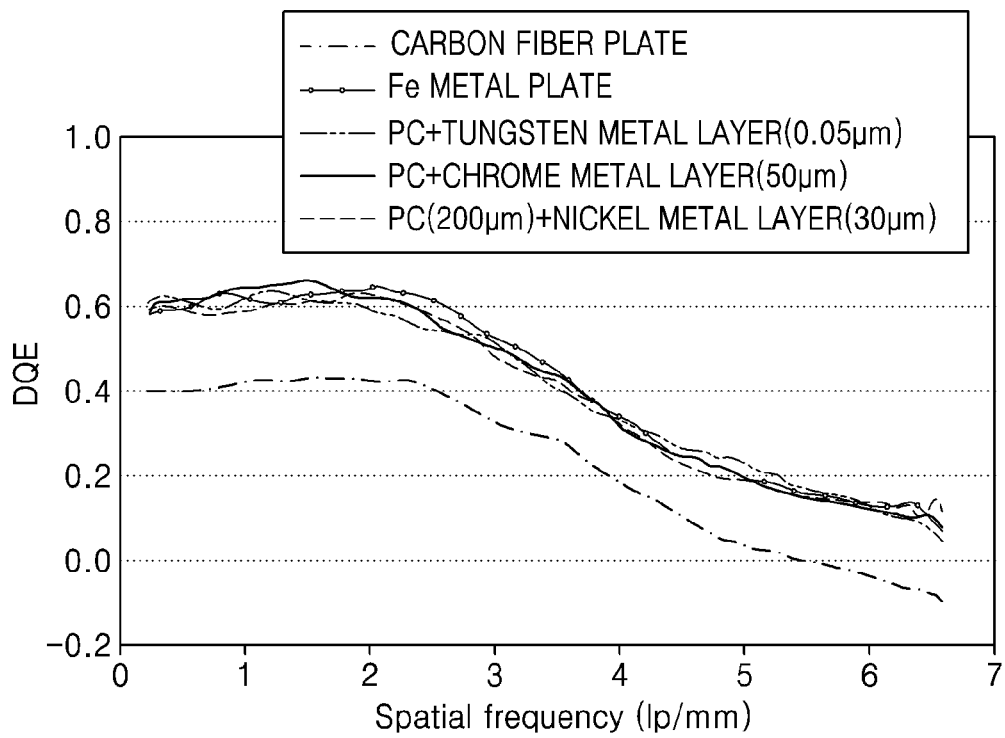
FIG. 3 is a graph illustrating, for each material of an intermediate plate, the detective quantum efficiency (DQE) of a radiation detector according to spatial frequency.

FIG. 3 is a graph illustrating, for each material of the intermediate plate, the detective quantum frequency (DQE) of the radiation detector 1 according to spatial frequency. Thereby, the grounding performance according to the material and thickness of the intermediate plate 200 may be known.

The detective quantum efficiency (DQE) is a physical approach for a common description of the imaging performance comparing the signal-to-noise ratio (SNR) of the image to the SNR of the radiation field, and a DQE value of 1 represents an ideal detector. A DQE value of 50% indicates that the detector of interest requires twice the absorbed dose to generate the image having an equivalent signal-to-noise fidelity as the ideal detector. The DQE is typically given as a function of the spatial frequency.

Moreover, all of the signals of the spatial frequency may be expanded into harmonic pulses (sine and cosine). The image may be interpreted as a combination of an infinite number of sine and cosine waves. A short wavelength (equivalent to a high spatial frequency) is related to a small detail in the image, and conversely, a long wavelength (equivalent to a low spatial frequency) is related to a large object. The relationship between the spatial frequency and the detail size is an inversely proportional relationship. 'Spatial frequency' is used to avoid confusion with the term 'time frequency'. The typical unit is line pairs per millimeter (1 p/mm).

In FIG. 3, the Fe metal plate is the Fe metal plate forming, by itself, the intermediate plate 200, and although the radiation transmittance is close to 0% due to the large thickness of the Fe metal plate, the grounding properties are excellent due to the high electrical conductivity, and thus the Fe metal plate was used as the reference for comparing the detection quantum efficiency (DQE) of the radiation detector 1 with respect to the intermediate plate 200 made of other materials.

When considering the Fe metal plate as the reference, it is observed that in the cases in which tungsten (W) is formed to a thickness of 0.05 μm (50 nm) on the back surface of the base plate 210 made of polycarbonate (PC), chrome (Cr) is formed to a thickness of 50 μm on the back surface of the base plate 210 made of polycarbonate (PC), and nickel (Ni) is formed to a thickness of 30 μm on both surfaces of the base plate 210 that is made of polycarbonate (PC) and has a thickness of 200 μm, the performance of the detection quantum efficiency (DQE) according to the spatial frequency exhibits similar characteristics to the case in which the Fe metal plate is used. Thus, it was observed that even when 30 nm to 1000 μm of the metal layer was formed on the surface of the base plate, excellent grounding properties were observed such as when using the intermediate plate formed of only the thick Fe metal plate.

Conversely, in the case of a carbon fiber plate that excludes the first metal layer and forms the intermediate plate 200 by using only carbon fiber, the performance of the detection quantum efficiency (DQE) is observed to be significantly lower than the Fe metal plate. The electrical conductivity of the carbon fiber included in the carbon fiber plate is about 0.06 S/m, and it may be observed that in the case of the intermediate plate having about this level of an electrically conductive property, the sufficient grounding performance may not be obtained. Likewise, when the thickness of the first metal layer of the intermediate plate is thinner than 30 nm, the sufficient electrical conductivity and resulting grounding performance may not be obtained, due to the boundary properties.

Therefore, in the present invention, the base plate including the carbon fiber or plastic with the high radiation transmittance, and the first metal layer disposed on a surface of the base plate were formed such that the intermediate plate was able to have the sufficient electrically conductive properties and the stable grounding properties. Here, the minimum thickness of the first metal layer 220 may be 0.03 μm in order to realize the stable grounding. That is, the thickness of the first metal layer of the intermediate plate may be at least 30 nm and at most the thickness at which the absolute radiation transmittance of the intermediate plate with respect to the radiation generated by the tube voltage of 20 to 35 kVp is at least 30%. For example, when tungsten is plated to a thickness of 0.03 μm to form the first metal layer, the absolute radiation transmittance of x-rays is high, being 89.77%, and the grounding properties are also excellent, and thus it is observed that this tungsten plating may be used as the first metal layer of the intermediate plate.

Figure 4:
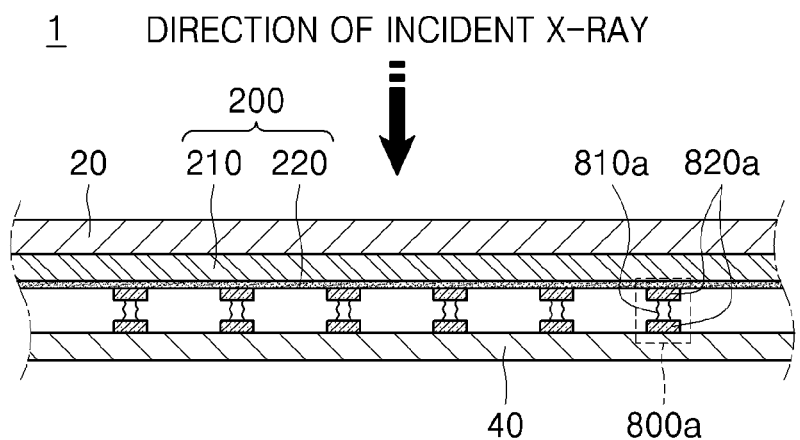
FIG. 4 is a cross-sectional view illustrating an embodiment in which a conductive connecting part electrically connects the ground line of a printed circuit board to a first metal layer.
Figure 5:
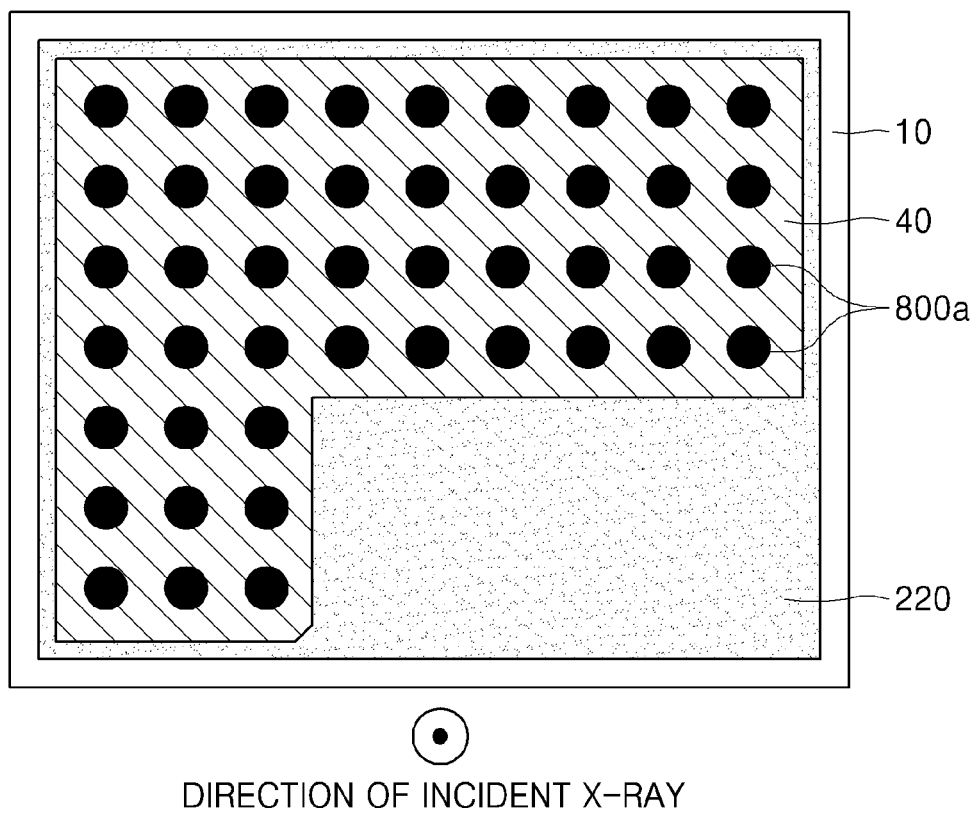
FIG. 5 is a plan view illustrating an embodiment in which a conductive connecting part electrically connects the ground line of a printed circuit board to a first metal layer.

FIG. 4 is a cross-sectional view illustrating an embodiment in which the conductive connecting part 800*a* electrically connects the first metal layer 220 to the ground line of the printed circuit board 40. FIG. 5 is a plan view illustrating an embodiment in which the plurality of conductive connecting parts 800*a* electrically connect the first metal layer 220 to the ground line of the printed circuit board 40 in a uniform manner.

Referring to FIG. 4, the plurality of conductive connecting parts 800*a* electrically connect the first metal layer 220 to the ground line of the printed circuit board 40, and may be spaced away from each other to be provided uniformly on the printed circuit board 40. Moreover, the conductive connecting part 800*a* may include a body part 810*a* connected to the printed circuit board 40 and extending toward the intermediate plate 200 and may further include a contacting part 820*a* having a larger cross-sectional area than the body part 810*a* and forming a contact surface with the printed circuit board 40 and the first metal layer 220. Here, the contacting part 820*a* may form the contact surface that is at least partially parallel to the first metal layer 220.

The body part 810*a* may be composed of an elastic member such as a spring or a clip. Since the body part 810*a* may be composed of the elastic member, the body part 810*a* may provide elasticity to the contacting part 820*a* such that when the body part 810*a* is compressed between the intermediate plate 200 and the printed circuit board 40, the contacting part 820*a* is pressed onto the intermediate plate 200 to form an electrically stable contact.

The body part 810*a* may be fixedly connected to the ground line of the printed circuit board 40 through soldering, and the like, and since the body part 810*a* may be applied, without a separate fabrication process, merely by making contact, the printed circuit board 40 and the intermediate plate 200 may be assembled or fabricated with ease. Meanwhile, since the body part 810*a* is connected to the intermediate plate 200 through the contacting part 820*a*, there is also no danger of the body part 810*a* protruding from the intermediate plate 200 to damage the radiation detection panel 20.

The contacting part 820*a* has a larger cross-section than the cross-section of the body part 810*a*, and may form the contact surface with the printed circuit board 40 and the first metal layer 220 to increase the contact area and thereby reduce the contact resistance. Since the resistance is inversely proportional to the contact area, the contacting part 820*a* may reduce the contact resistance by maximizing the surface area that is at least partially parallel to the printed circuit board 40 and the first metal layer 220.

Referring to FIG. 5, in order to minimize the ground loop noise, the plurality of conductive connecting parts 800*a* may be spaced apart to be uniformly disposed as a plurality and electrically connect the ground line of the printed circuit board 40 to the first metal layer 220 formed on the back surface of the intermediate plate 200. As described above, the ground loop noise caused by the potential difference due to the change in loop distance between the grounds may be minimized to allow the electric signal in the radiation detection panel 20 to gain stability with respect to the ground loop noise. For this, the first metal layer 220 that is formed on the back surface of the base plate 210 as the reference potential of the printed circuit board 40 may be used as the ground to minimize the separation distance with the printed circuit board 40. Moreover, the ground must be connected to all of the frame of the housing 10, the first metal layer 220, the ground line of the printed circuit board 40, and the ground line of the radiation detection panel 20. In addition, in order to minimize the ground loop noise, the conductive connecting parts 800*a* may connect the first metal layer 220 to the printed circuit board 40 numerous times in a uniform manner.

Figure 6:
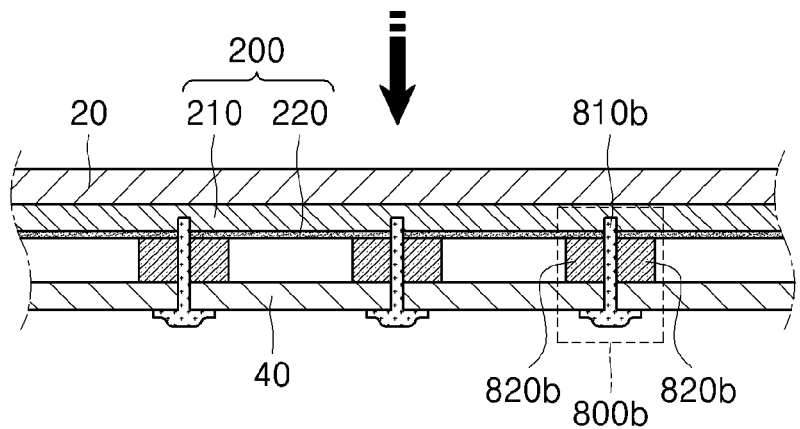
FIG. 6 is a cross-sectional view illustrating another embodiment in which a conductive connecting part electrically connects the ground line of a printed circuit board to a first metal layer.

FIG. 6 is a cross-sectional view illustrating another embodiment in which the conductive connecting part 800*b* electrically connects the first metal layer 220 to the ground line of the printed circuit board 40. The body part 810*b* penetrates through the printed circuit board 40 and may extend toward the intermediate plate 200 to couple the printed circuit board 40 to the intermediate plate 200. The body part 810*b* may be made of metal, which is a thermally and electrically conductive material. The body part 810*b* may be a bolt provided with a part that penetrates through the printed circuit board 40 and a catching part that is on the head and is larger than the through-hole.

Meanwhile, as the middle of the contacting part 820*b* is penetrated by the body part 810*b* and thereby coupled to the contacting part 820*b*, the contacting part 820*b* may have a larger contact area with the printed circuit board 40 on a contact region of the intermediate plate 200. Therefore, the contact resistance may be reduced in an inversely proportional manner to the increased contact area. Here, the contacting part 820*b* may be a metal ring or have the form of a disk. Moreover, as illustrated in FIG. 6, the contacting part 820*b* may be formed as the metal ring between the printed circuit board 40 and the intermediate plate 200 to maintain a fixed distance between the printed circuit board 40 and the intermediate plate 200.

Here, as illustrated in FIG. 5, in order to minimize the ground loop noise, the plurality of connecting parts 800*b* may electrically connect the first metal layer 220 to the ground line of the printed circuit board 40 in a uniform manner.

Figure 7:
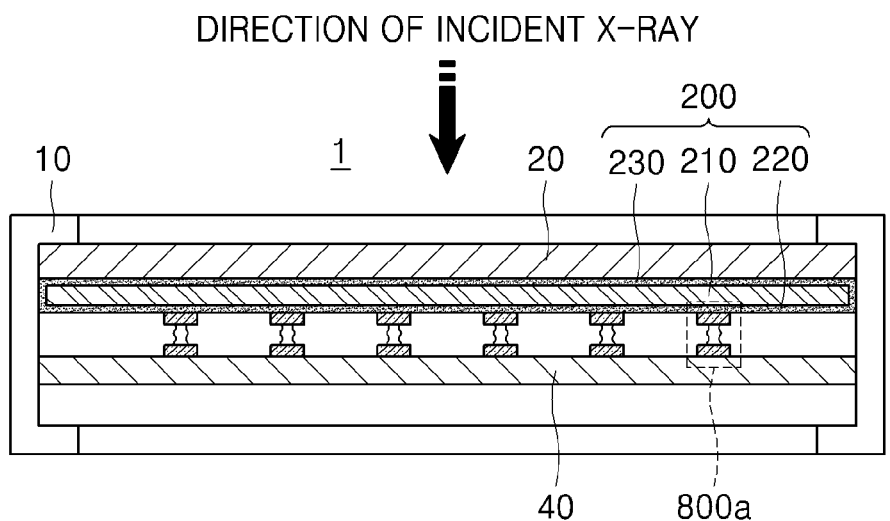
FIG. 7 is a cross-sectional view of a radiation detector according to another embodiment of the present invention.

FIG. 7 is a cross-sectional view of a radiation detector 1 according to another embodiment of the present invention. Referring to FIG. 7, the intermediate plate 200, as described above, may further include the base plate 210 composed of the carbon fiber layer or of at least one plastic, having an excellent radiation transmittance, selected from among a carbon fiber reinforced plastic or polycarbonate, and the like; the first metal layer 220 provided on the back surface of the base plate 210; and the second metal layer 230 provided on the front surface and electrically connected to the first metal layer 220. Thus, the intermediate plate 200 may further include the second metal layer 230, which is electrically connected to the first metal layer 220 and provided on the front surface, to further strengthen the grounding function through the first metal layer 220.

Moreover, as described above, by forming the second metal layer 230 on the front surface, which is close to the radiation detection panel 20, of the base plate 210, the ground line of the radiation detection panel 20 may be electrically connected to the second metal layer 230 to minimize the loop distance between the grounds and thereby minimize the ground loop noise. Meanwhile, the ground may be connected to all of the frame of the housing 10, the first metal layer 220 of the intermediate plate, the second metal layer 230, the ground line of the printed circuit board 40, and the ground line of the radiation detection panel 20 such that the ground potentials are the same.

In addition, the first metal layer 220 may be both thermally and electrically connected to the second metal layer 230 at an edge region of the intermediate plate 200. In this case, the heat conducted to the first metal layer 220 may be conducted to the second metal layer 230 to generate thermal noise at the edge region of the radiation detection panel 20. However, the thermal noise generated at the edge region does not have a large effect on the overall radiation picture image and thus may be disregarded.

Figure 8:
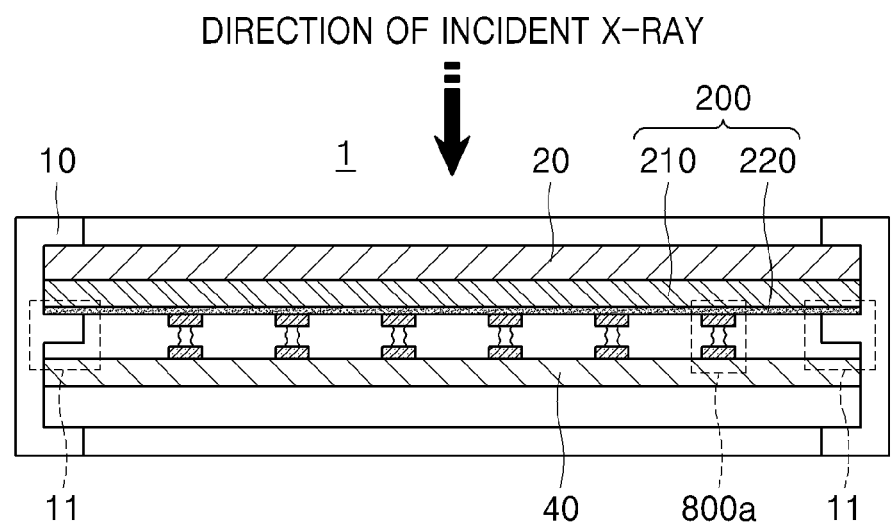
FIG. 8 is a cross-sectional view of a radiation detector according to another embodiment of the present invention.

FIG. 8 is a cross-sectional view of a radiation detector 1 according to another embodiment of the present invention. The housing 10 may include the frame made of gold, and may further include a supporting part 11 extending from the frame and supporting the intermediate plate 200. Moreover, the supporting part 11 may be coupled to the intermediate plate 200, contacting with the intermediate plate 200 by way of surface contact. Thus, the supporting part 11 may reduce the contact resistance in a manner that is inversely proportional to the contact area, contacting with the back surface or the front surface of the intermediate plate by way of surface contact.

Since the first metal layer 220, which is provided on the back surface of the intermediate plate 200 and has a high thermal conductivity, makes surface contact with the supporting part 11, the heat generated in the elements of the printed circuit board 40 may pass through the first conductive layer 220 through the conductive connecting part 800*a* to be transferred to the supporting part 11.

Meanwhile, the printed circuit board 40 may have a different shape than a typical rectangular printed circuit board in order to process low noise data from the radiation detection panel 20, shorten the signal processing path between electronic components configured for high-speed data transfer, and enhance the integration efficiency with the read out integrated circuits disposed at the edge of one side of the printed circuit board 40. That is, unlike the shape of the typical rectangular printed circuit board, parts, other than a region in which the read out integrated circuits (read out IC) and gate integrated circuits (gate IC) are disposed, a region in which a power over Ethernet (POE), a field programmable gate array (FPGA), an embedded CPU, a memory, an Ethernet physical interface & tranceiver, a power element, and related elements are disposed, and a region that is near the read out integrated circuit and the gate integrated circuit and in which are disposed, on both sides of the printed circuit board, a filter element, a connector, and related components, may be removed from the printed circuit board. Here, the printed circuit board 40 may be L-shaped or reverse L-shaped. By removing unneeded parts from the printed circuit board as such, it is possible to effectively reduce the weight of the printed circuit board and the radiation detector.

Moreover, a plurality of electronic components electrically connected to the radiation detection panel 20 may be mounted on both surfaces of the printed circuit board 40. For example, the plurality of electronic components may be passive element or active element components that constitute a data processing circuit, a power driver circuit, or a control circuit, and the like. Here, in order to minimize, in the radiation detection panel 20, the noise caused by heat, active element components (FPGA, CPU, etc.) that generate a lot of heat and passive element components having a high height may be disposed on the back surface of the printed circuit board 40. Power element components may be prioritized to be disposed on the back surface of the printed circuit board 40 in order to minimize noise. Therefore, the electromagnetic interference noise that affects the radiation detection panel 20 in the radiation detector 1 may be minimized.

Likewise, the field programmable gate array (FPGA), the embedded CPU, the power element, and the related components generate a lot of electromagnetic interference (EMI) noise and power noise, and thus may be disposed in a region that is spaced as far apart as possible from the read out integrated circuit in order to minimize the effects of the electromagnetic interference (EMI), and the like, on the read out integrated circuit. In addition, the connectors in the Ethernet physical interface & tranceiver, and the POE, and the like, must protrude to the outside of the radiation detector 1 in order to be connected to an external cable, and thus may be disposed in a region that is on the opposite surface to an insertion surface on which the cassette-shaped radiation detector 1 is inserted into the radiography apparatus.

Since the gate integrated circuit (gate IC) is disposed at a close distance to the power over Ethernet (POE), the field programmable gate array (FPGA), the embedded CPU, the memory, the Ethernet physical interface & tranceiver, the power element, and the related components, a decline in speed and an input power noise may be minimized during high-speed data transmission.

The radiation detector 1 may further include the filter element, the connector, and the related components on both surfaces of a region, in the printed circuit board 40, near the read out integrated circuit and the gate integrated circuit.

In particular, among the electronic components mounted on the printed circuit board 40, the read out integrated circuit (ROIC: read out IC) is a semiconductor that selects/drives the electric signal converted by the radiation detection panel 20, and may include an amp in order to amplify weak analog signals coming from the radiation detection panel 20. Furthermore, according to advances in integration techniques, in addition to the amp, an analog digital convertor (ADC) may also be included to convert analog values to digital values. Therefore, the read out integrated circuit consumes a large amount of current and power, and thus generates a large amount of heat. When such heat is transferred to the radiation detection panel 20, the operating temperature of the radiation detection panel 20 increases. Accordingly, the dark current in the photoelectric conversion element and the leakage current in the TFT are increased and the amount of fixed noise is changed, and thus there is a problem that causes an image unbalance. Consequently, it is necessary to release the heat generated in the read out integrated circuit 30 and the other electronic components in order to prevent this heat from being transferred to the radiation detection panel 20.

Meanwhile, the thermal conductivity of the base plate 210 of the intermediate plate 200 may be lower than the thermal conductivity of the first metal layer 220 provided on the back surface of the intermediate plate 200. For example, at 300 K, the thermal conductivity of the polycarbonate (PC) that may be used as the base plate 210 is 0.19 to 0.22 W/(m·K), and the thermal conductivity of aluminum (Al) is 237 W/(m·K). Thus, the heat generated in the printed circuit board 40 is only transferred to the first metal layer 220, and it is difficult for the heat to be transferred to the base plate 210.

The housing 10 may include the frame composed of metal, and may further include the supporting part 11 that extends from the frame to support the intermediate plate 200. Moreover, the supporting part 11 may be coupled to the back surface of the intermediate plate 200, contacting with the back surface of the intermediate plate 200 by way of surface contact.

Therefore, the heat transferred to the first metal layer 220 may be transferred to the supporting part 11 extending from the frame of the housing 10 to be released to the outside through the frame of the housing 10. Thereby, the noise due to the heat that is transferred to the radiation detection panel 20 may be reduced.

As in the present invention, by forming the first metal layer on the back surface of the intermediate plate 200, not only may the separation distance between the printed circuit board 40 and the intermediate plate 200 be reduced to minimize the ground loop noise, but also the heat generated from the electronic components mounted on the printed circuit board 40 may not be transferred to the radiation detection panel and may instead be released to the outside through the first metal layer.

As described in FIG. 6, in order to maximize the heat releasing effect, the shape of the contacting part 820b of the conductive connecting part 800b may be the shape that enables the maximum heat releasing effect (for example, the shape having numerous bumps for releasing heat).

The supporting part 11 may be coupled to the back surface of the intermediate plate 200 at the edge region of the intermediate plate 200, and the area of the radiation detection panel 20 may be smaller than the area of the intermediate plate 200. Thus, the heat in the first metal layer 220 may be transferred to the second metal layer 230, which is connected to the edge region of the first metal layer 220, such that even when the thermal noise that is generated is limited to the edge region of the radiation detection panel 20, the effect on the overall radiation picture image is not large and thus may be disregarded.

FIG. 9 is a front elevation of a radiography apparatus 1000 according to another embodiment of the present invention, and FIG. 10 is a side elevation of the radiography apparatus 1000 according to another embodiment of the present invention.

Describing the radiography apparatus 1000 according to another embodiment of the present invention in more detail by referring to FIGS. 9 and 10, duplicate elements that were described with respect to the radiation detector 1 according to an embodiment of the present invention will be excluded.

The radiography apparatus 1000 may include the radiation generator 1100, a breast holding part 1200, the radiation detector 1 according to the present invention, the automatic exposure control sensor 1300, and a controller 1400.

The radiation generator 1100 emits radiation toward the object disposed on the radiation detector 1, and this may also be performed by using a widely known technique. The radiation generator 1100 is connected to the automatic exposure control sensor 1300 of the radiation detector 1, and the radiant exposure may be regulated by the controller 1400. Meanwhile, the radiography apparatus 1000 may be a mammography apparatus that holds the chest (or breast) of a person.

The breast holding part 1200 is an instrument that holds the breast so that the breast does not move during the radiography, and holds the breast to be perpendicular to the direction in which the radiation is emitted by compressing the breast of the patient from both directions. Typically, a support plate is installed below, and a compression plate is installed above such as to be capable of being raised and lowered.

The automatic exposure control sensor 1300 may detect, among the radiation emitted from the radiation generator 1100, the radiation passing through the radiation detector 1. As described above, the automatic exposure control sensor 1300 may be disposed in an empty region of the printed circuit board 40 such that, in the radiation detector 1, the transmission of radiation is not hindered by the electronic components such as the read out integrated circuit.

Next, the controller 1400 may regulate the exposure dose of radiation emitted from the radiation generator 110 according to the radiation dose detected in the automatic exposure control sensor 1300.

Meanwhile, the radiography apparatus 1000 may also be the computer radiography (CR) mammography apparatus. Here, the radiation detector 1 according to the present invention is inserted instead of the computer radiography (CR) mammography cassette. When the radiation detector 1 according to the present invention is installed in the computer radiography (CR) mammography apparatus, a sufficient radiation dose may be transmitted on the automatic exposure control sensor 1300 in order to prevent a decrease in the radiation detection capability of the automatic exposure control sensor 1300 included in the computer radiography (CR) mammography apparatus. Therefore, the radiation detector 1 may be compatible for use in the computer radiography (CR) apparatus.

As described above, the radiation detector 1 according to the present invention may obtain a stable image by forming the metal layer 220 on the back surface to shield the noise due to the electromagnetic interference noise and the noise due to the heat, which are generated in the electronic components mounted on the printed circuit board 40, and by providing the intermediate plate 200 that is connected to the ground line of the printed circuit board 40 to form the ground potential and the shield.

Moreover, the separation distance between the intermediate plate 200, which is formed as the ground, and the ground line of the printed circuit board 40 may be minimized to thereby minimize the ground loop noise. Thus, an even more stable radiation image may be obtained.

In addition, in the radiation detector 1 according to an embodiment of the present invention, the first metal layer 220 provided on the back surface of the base plate 210 included in the intermediate plate 200 may be connected to the frame of the housing 100 such that the heat generated in the printed circuit board 40 may be effectively released to the outside through conduction.

Therefore, since the radiation detector 1 according to the present invention may effectively release the heat generated during operation to block the heat from being conducted to the radiation detection panel 20, the noise caused by heat may be removed from the image. Thus, the radiation detector 1 according to the present invention may obtain the stable and sharp radiation picture image.

Consequently, the radiation detector 1 according to an embodiment of the present invention may be designed as a small, film-type digital radiography (DR) mammography cassette capable of maintaining high robustness and noise tolerance.

What is claimed is:

1. A radiation detector, comprising:
   a housing;
   a radiation detection panel accommodated in the housing and converting radiation incident from the outside of the housing into an electric signal;
   a printed circuit board electrically connected to the radiation detection panel; and
   an intermediate plate that is disposed between the radiation detection panel and the printed circuit board, supports the radiation detection panel, and is electrically connected to a ground line of the printed circuit board,
   wherein the intermediate plate comprises a base plate and an electrically conductive first metal layer formed in a shape of a blanket film having a thickness of 0.03 to 1,000 μm, and the intermediate plate is transmissive to the radiation, and is formed as a conductive plate, and
   wherein the radiation is uniformly reflected over the surface of the intermediate plate by the first metal layer.

2. The radiation detector of claim 1, wherein an absolute radiation transmittance of the intermediate plate, with respect to the radiation generated by a tube voltage of 20 to 35 kVp, is 30% or higher.

3. The radiation detector of claim 1, wherein a plurality of electronic components electrically connected to the radiation detection panel are mounted on both surfaces of the printed circuit board.

4. The radiation detector of claim 1,
   wherein the intermediate plate is transmissive to x-ray radiation in the range of 20 to 35 KeV.

5. The radiation detector of claim 1,
   wherein an absolute radiation transmittance of the intermediate plate to x-ray radiation in the range of 20 to 35 KeV is 30% or higher.

6. The radiation detector of claim 1,
   wherein the ground potential of the electrically conductive first metal layer is uniform with the with the ground potential of the printed circuit board.

7. The radiation detector of claim 1,
   wherein the electrically conductive first metal layer provides a uniform reflection of light to the radiation detector.

8. The radiation detector of claim 1, wherein the housing comprises:
   a frame composed of metal; and
   a supporting part extending from the frame and supporting the intermediate plate,
   wherein the supporting part is coupled to the intermediate plate, contacting with the intermediate plate by way of surface contact.

9. The radiation detector of claim 8, wherein the supporting part is coupled to the intermediate plate at an edge region of the intermediate plate.

10. The radiation detector of claim 1, wherein the intermediate plate further comprises:
the base plate supporting the first metal layer; and
wherein the electrically conductive first metal layer is electrically connected to the ground line of the printed circuit board.

11. The radiation detector of claim 10, further comprising a plurality of conductive connecting parts provided spaced apart from each other and electrically connecting the first metal layer to the ground line of the printed circuit board,
wherein each of the conductive connecting parts comprises:
a body part connected to the printed circuit board and extending toward the intermediate plate, and
a contacting part having a larger cross-sectional area than the body part and forming a contact surface with the first metal layer.

12. The radiation detector of claim 10, wherein a thermal conductivity of the base plate is lower than a thermal conductivity of the first metal layer.

13. The radiation detector of claim 10, wherein the base plate comprises at least one of carbon fiber or plastic, and the first metal layer is provided on a back surface of the base plate.

14. The radiation detector of claim 13, wherein the intermediate plate further comprises a second metal layer provided on a front surface of the base plate and electrically connected to the first metal layer.

15. The radiation detector of claim 14, wherein the first metal layer is electrically connected to the second metal layer at an edge region of the intermediate plate.

16. A radiography apparatus, comprising:
a radiation generator;
the radiation detector of claim 1 which is detecting radiation emitted from the radiation generator;
an automatic exposure control sensor sensing, among radiation emitted from the radiation generator, the radiation passing through the detector; and
a controller to control an exposure dose of the radiation emitted from the radiation generator according to a radiation dose sensed by the automatic exposure control sensor.

17. A radiation detector, comprising:
a housing;
a radiation detection panel accommodated in the housing and converting radiation incident from the outside of the housing into an electric signal;
a printed circuit board electrically connected to the radiation detection panel; and
an intermediate plate that is disposed between the radiation detection panel and the printed circuit board, supports the radiation detection panel, and is electrically connected to a ground line of the printed circuit board,
wherein the intermediate plate comprises a base plate and an electrically conductive first metal layer that is formed in a shape of a blanket film and is electrically connected to the ground line of the printed circuit board, and
the intermediate plate is transmissive to the radiation, and is formed as a conductive plate, and
wherein the radiation is uniformly reflected over the surface of the intermediate plate by the first metal layer.

18. The radiation detector of claim 17, wherein an absolute radiation transmittance of the intermediate plate, with respect to the radiation generated by a tube voltage of 20 to 35 kVp, is 30% or higher.

19. The radiation detector of claim 17, wherein the intermediate plate further comprises:
the base plate supporting the first metal layer.

20. The radiation detector of claim 19, further comprising a plurality of conductive connecting parts provided spaced apart from each other and electrically connecting the first metal layer to the ground line of the printed circuit board,
wherein each of the conductive connecting parts comprises:
a body part connected to the printed circuit board and extending toward the intermediate plate, and
a contacting part having a larger cross-sectional area than the body part and forming a contact surface with the first metal layer.

21. The radiation detector of claim 19, wherein a thermal conductivity of the base plate is lower than a thermal conductivity of the first metal layer.

22. The radiation detector of claim 19, wherein the base plate comprises at least one of carbon fiber or plastic, and the first metal layer is provided on a back surface of the base plate.

23. The radiation detector of claim 22, wherein the intermediate plate further comprises a second metal layer provided on a front surface of the base plate and electrically connected to the first metal layer.

24. The radiation detector of claim 23, wherein the first metal layer is electrically connected to the second metal layer at an edge region of the intermediate plate.

25. A radiation detector, comprising:
a housing;
a radiation detection panel accommodated in the housing and converting radiation incident from the outside of the housing into an electric signal;
a printed circuit board electrically connected to the radiation detection panel; and
an intermediate plate that is disposed between the radiation detection panel and the printed circuit board, supports the radiation detection panel, and is electrically connected to a ground line of the printed circuit board,
wherein the intermediate plate comprises a base plate and an electrically conductive first metal layer formed in a shape of a blanket film having a thickness of 0.05 to 1,000 μm, and the intermediate plate is transmissive to 30% or higher of radiation in the range 20 to 35 KeV, and the intermediate plate is formed as a conductive plate, and
wherein the radiation is uniformly reflected over the surface of the intermediate plate by the first metal layer.

* * * * *